United States Patent [19]

Stockton et al.

[11] Patent Number: 4,569,947
[45] Date of Patent: Feb. 11, 1986

[54] β-BRANCHED ALCOHOL MOSQUITO CONTROL AGENT

[75] Inventors: James R. Stockton, Delaware; Richard C. Dodwell, Powell, both of Ohio

[73] Assignee: Sherex Chemical Company, Inc., Dublin, Ohio

[21] Appl. No.: 670,637

[22] Filed: Nov. 13, 1984

[51] Int. Cl.$^4$ .................. A01N 31/00; A01N 31/04
[52] U.S. Cl. ................... 514/724; 514/722; 514/723
[58] Field of Search ............... 424/342, 343; 514/724, 514/722, 723

[56] References Cited

U.S. PATENT DOCUMENTS 4,160,033  7/1979  Garrett et al. ................. 424/285

Primary Examiner—Leonard Schenkman
Attorney, Agent, or Firm—Mueller and Smith

[57] ABSTRACT

Disclosed is an improved method for controlling mosquitos wherein a body of water containing immature forms of mosquitos has its surface coated with a thin film of a control agent which is a non-ionic, organic material with a density less than that of water. The improvement in such method comprises coating the surface with an approximately monomolecular film of a β-branched alcohol of the following structure:

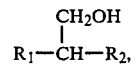

where
$R_1$ and $R_2$ is $C_9-C_{28}$; and
$R_1$ and $R_2$ is at least $C_3$, or
$R_2$ is $CH_3$ and $R_1$ has at least two branch sites.

18 Claims, No Drawings

β-BRANCHED ALCOHOL MOSQUITO CONTROL AGENT

BACKGROUND OF THE INVENTION

The present invention relates to the control of mosquitos by application to breeding waters of film-forming materials and more particularly to providing a new control agent therefor.

An important development in mosquito control in preventing emergence of the adult from its aquatic breeding site is reported by Garrett in U.S. Pat. No. 4,160,033. The method reported involves the application of an approximately monomolecular film of a non-ionic, autophobic, organic material with a density less than that of water, a boiling point of 170° C. or higher, a freezing point of less than 5° C., and HLB number of 10 or less, a bulk viscosity of less than 1,000 centistokes at the temperature of use, a spreading velocity of 10 cm/sec. for the first 100 cm, and a lowering of the surface tension of the surface of the water to 30 dynes/cm or less. Those organic materials or control agents which fit the foregoing definition can be selected from sorbitan mono-oleate; saturated, branched chain alcohols with a carbon total of from 15 to 19 carbon atoms and 1 to 3 oxyethylene groups; unsaturated alcohols with 15–19 carbon atoms chain length; unsaturated ethers with a chain length of from 12–18 carbon atoms and 3–5 oxyethylene groups; and oleyl ether with two oxyethylene groups; and mixtures thereof.

BROAD STATEMENT OF THE INVENTION

The present invention is an improved method for controlling mosquitos wherein a body of water containing immature forms of mosquitos has its surface coated with an approximately monomolecular film of a liquid control agent which is non-ionic, autophobic, and an organic material with a density of less than that of water. The improvement in such method comprises applying to said body of water an effective amount of a β-branched alkanol of the following structure:

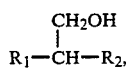

where the total carbon atoms of $R_1$ and $R_2$ range from between about 9 and 28. Advantageously, one of the R groups contains at least three carbon atoms and preferably at least five. Alternatively, if $R_2$ is a methyl group, then $R_1$ should be highly branched, eg. containing at least two or more branch sites. The surface tension of water coated with the β-branched alkanols of the present invention is greater than 35 and typically between about 40 and 50 dynes/cm.

While the β-branched alkanols of the present invention quite unexpectedly provide effective kill of immature mosquitos, the activity of the β-branched alkanols can be enhanced markedly by forming the alkoxylates thereof. Accordingly, β-branched primary alkanol alkoxylates is another class of mosquito control agents of the present invention. Advantageously, the alkoxylate substituent is formed from between about 1 and 3 moles of ethylene oxide. Alternatively, a mixture of ethylene oxide and propylene oxide may be used for forming the alkoxylate control agents of the present invention. The β-branched primary alkanol or its alkoxylate may be supplied neat, dispersed in a solvent for enhancing its fluidity, or may be supplied in a solid matrix for its continual release over extended periods of time.

The present invention is based upon the unexpected discovery that certain alcohols are effective in the control of mosquitos despite the art teaching against their use. The alkoxylate control agents of the present invention are dramatically more efficacious than any control agent heretofore evaluated. An advantage is that the control agents of the present invention appear to be ostensibly non-toxic in the environment and not injurious to non-target species. These and other advantages will be readily apparent to those skilled in the art based upon the disclosure contained herein.

DETAILED DESCRIPTION OF THE INVENTION

A precise explanation for the efficacy which the β-branched alkanols display cannot be given, though certainly the high degree of branching of such alkanols seems to contribute to such efficacy. As noted above, Garrett teaches that the control agents must lower the surface tension of the surface of water to 30 dynes/cm or less in order to be effective in the control of immature forms of mosquitos. The β-branched alkanols of the present invention, however, provide surface tensions which are much greater than 30 dynes/cm and typically can range from between about 40 and 50 dynes/cm. That the β-branched alkanols of the present invention function in the control of mosquitos is taught away from by the Garrett patent.

As to the alkoxylate derivatives of the β-branched primary alkanols, their physical properties, including lowering the surface tension of water to less than 30 dynes/cm, are within the scope of the broad disclosure of the Garrett patent; however, the precise alkoxylates of the present invention are not taught therein. Quite unexpectedly, the class of alkoxylate control agents of the present invention provide more enhanced mosquito control than does any control agent heretofore taught and tested by the art. Presumably, the unexpected effectiveness of the alkoxylate control agents of the present invention, at least in part, is based on the fact that they are derived from a class of alkanols which are totally unexpected to possess mosquito control functionality. The examples will fully confirm the efficacy of all control agents of the present invention.

Broadly, the β-branched alkanol control agents of the present invention can be represented by the following general chemical formula:

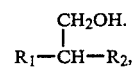

The total number of carbon atoms of $R_1$ and $R_2$ should range from about 9 to about 28. If $R_2$ is a methyl group, then $R_1$ should be a highly branched chain, eg. having at least two or more branch sites. When $R_2$ is a longer alkyl substituent, then the need for a multiplicity of branching of the $R_1$ substituent is not important as the high degree of branching of the alcohol control agent is provided by the β-branching itself. Advantageously, $R_2$ will be at least a $C_3$ group and advantageously at least a $C_5$ group with the balance of the carbon atoms existing in $R_1$. The examples will further illustrate suitable β-branched alkanol control agents useful in the control of mosquitos.

Two techniques for synthesizing the β-branched alkanol control agents of the present invention can be envisioned readily. The presently preferred synthetic technique is that of a Guerbet alkanol. Details of the Guerbet conversion may be found in March, *Advanced Organic Chemistry*, Second Edition, pp 1114–1115, McGraw-Hill, Inc., New York, N.Y. (1977). Primary alcohols couple to form β-branched alkanols when treated with sodium (or another base) and copper-bronze, Raney nickel or other hydrogenation catalysts. This Guerbet reaction involves three molecules of the feed alcohol, one of which is oxidized to the acid.

The second technique readily envisioned for forming the β-branched alkanol control agents of the present invention is the conventional "oxo process". Hydroformylation or the "oxo process" may be used to convert an internal olefin to a β-branched alkanol in the presence of carbon monoxide, hydrogen, and a catalyst which may be a cobalt carbonyl, rhodium complex, or other transition-metal compound. Further details on the oxo process may be found in March, *Advanced Organic Chemistry*, p 738 (supra). Currently, the oxo process is a well-known and often practiced commercial process.

The alkoxylate derivatives of the β-branched primary alkanols are formed in conventional fashion, preferably using between about 1 and 3 moles of ethylene oxide per mole of alkanol. Alternatively, a mixture of ethylene oxide and propylene oxide may be used for forming the alkoxylate control agents of the present invention. These alkoxylate control agents possess the general characteristics of the control agents taught in the Garrett patent, though the surface tensions of water tend to be lowered to lower values than is accomplished by the control agents of the Garrett patent. As the examples will demonstrate, unexpectedly the class of alkoxylate control agents of the present invention provide superior control of mosquitos than is attainable by use of the control agents of the Garrett patent. Note that such alkoxlates typically are mixtures of β-branched alkanols and its alkoxylate, especially at low molar ratios of alkylene oxide to β-branched alkanol. Such alkoxylate/alkanol mixtures display efficacy in mosquito control also.

Most of the control agents of the present invention are sufficiently fluid so that they may be used neat on bodies of water for the control of mosquitos. However, the control agents may be blended with other control agents or with solvents for enhancing their fluidity for practical use and application. In this regard, it should be understood that the control agents of the present invention additionally may be supplied in combination with a solid matrix as disclosed in commonly-assigned application of Richard R. Egan, entitled "Mosquito Control Agent in Solid Form", U.S. Ser. No. 06/375,864, filed May 7, 1982. Use of the solid form mosquito control agent permits the mosquito population to be controlled over extended periods of time, substantially independent of numerous climatic conditions, such as, for example, dry spells during which the body of water may dry up, followed by its replenishment during later rainy periods. Note further that an alternative solid carrier for the mosquito control agent may be found in U.S. Pat. Nos. 3,846,404 and 3,985,298.

The following examples show how the present invention can be practiced but should not be construed as limiting. In this application, all proportions and percentages are by weight and all units are in the metric system, unless otherwise expressly indicated. Also, all citations referenced herein are expressly incorporated herein by reference.

IN THE EXAMPLES

Several β-branched alkanols were evaluated for efficacy in controlling mosquitos. These alkanols may be represented by the following general structures:

| Alcohol No. | Structure | Surface Tension* |
|---|---|---|
| M | $C_9H_{19}$\CH—$CH_2OH$ / $C_7H_{15}$ | 46 dynes/cm |
| H** | $(C_8H_{17}$—$C_{10}H_{21})$\CH—$CH_2OH$ / $(C_6H_{13}$—$C_8H_{17})$ | 45 dynes/cm |
| N | $CH_3$—$C(CH_3)(CH_3)$—$CH_2$—$CH(CH_3)$—$CH_2$—$CH_2$\CH—$CH_2OH$ / $CH_3$—$C(CH_3)(CH_3)$—$CH_2$—$CH(CH_3)$ | 48 dynes/cm |
| T | $CH_3$—$CH(CH_3)$—$CH_2CH(CH_3)$—$CH_2$—$CH(CH_3)$—$CH_2$\CH—$CH_2$—OH / $CH_3$ | 40 dynes/cm |

*Surface tension of water having its surface coated with the alkanol
**Mixture of $C_{16}$, $C_{18}$, $C_{20}$, 2-alkyl alkanols; homolog weight-percent distribution, $<C_{16}$ = 1%, $C_{16}$ = 14%, $C_{18}$ = 45%, $C_{20}$ = 34%, and $>C_{20}$ = 6%

These alcohols (and their 2 mole ethoxylates) were compared to commercial isostearyl alcohol (and its 2 mole ethoxylates; Adol 66 isostearyl alcohol, Sherex Chemical Company, Dublin, Ohio) (hereinafter often referred to as "comparative isostearyl alcohol" and "comparative ethoxylated isostearyl alcohol", respectively). This isostearyl alcohol is produced by the high pressure catalytic hydrogenation of isostearic acid which is followed by filtration and distillation. Based upon U.S. Pat. No. 2,812,342, isostearic acid is a by-product of dimer acid production (the thermal polymerization of tall oil or soybean acids). Isostearic acid is isolated from the unpolymerized hydrogenated portion via solvent separation.

A typical composition of isostearic acid is:

| Chain Length | Normal Acids (wt %) | Iso-Acids (Carbon No.) (wt %) |
| --- | --- | --- |
| $C_{14}$ | 1-3 | — |
| $C_{16}$ | 6-8 | 1-3 |
| $C_{18}$ | 8-10 | 60-66 |
| $C_{18:1}$ | — | 16-20 |

GLC analysis of isostearic acid yields a smear and exact identification of each peak is not possible. It is believed that the composition of the isostearic acid is primarily of the methyl branched series or

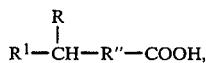

where R is methyl and the location of R varies in the 2 to 10 position as relates to stearic acid. Lesser amounts of certain cyclic acids probably are formed via isomerization of oleic acid:

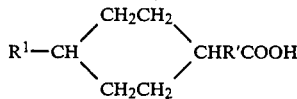

Isostearyl alcohol contains structures similar to the isostearic acids alkyl composition described above.

EXAMPLE 1

The mosquito controlling efficacy of β-branched alcohol N of the present invention was investigated and compared to the mosquito controlling efficacy of the isostearyl alcohol which contains the same number of carbon atoms as does β-branched alcohol N of the present invention. The physical properties of the alcohols evaluated are set forth below.

TABLE 1
PHYSICAL PROPERTIES OF ALCOHOLS

| Property | β-Branched Alcohol N | Isostearyl Alcohol |
| --- | --- | --- |
| Density | 0.836 g/cc | 0.857 g/cc |
| Surface Tension Reduction | 47.7 dynes/cm | 37.9 dynes/cm |
| Hydroxyl value | 195-210 | 194 |
| Iodine value | 3 max | 11 |
| Viscosity* | 114 cst (100° F.) | 67.7 cst (77° F.) |
| Acid value | 1 max | 0.3 |
| Saponification value | 2 max | 1.5 |

*centipoises = density × centistokes

Bioassays against larvae of *Aedes taeniorhynchus* (A.T.) and *Culex quinquefasciatus* (C.Q.) were conducted utilizing formulations of foregoing β-branched alcohol N and comparitive isostearyl alcohol in order to determine the mosquito controlling efficacy of such materials. Tests were conducted in 400 ml glass beakers containing 10 first-fourth instar larvae of Aedes and Culex spp and 250 ml of test water (three replications per test series). Controls (breeding beakers with no applied film) were used to monitor each test series. Test water for A.T. consisted of 12.5% artificial sea water (Instant Ocean ®) while water for the C.Q. was well-water purified by reverse osmosis (RO) filtration. Prior to introduction of the test formulations, larvae in each beaker were fed a few drops of ground rabbit chow-RO suspension.

Formulations were applied to the surface of the water with a microsyringe at the rate of 0.25 ml/m² (0.26 gal/acre) active ingredient in several tests. The beakers then were loosely covered with a sheet of clear polyethylene to retard evaporation and subsequent loss of test formulations on the sides of the beakers. The tests were conducted in a room maintained at 25±1° C. (ambient) and 80 percent relative humidity. Cumulative percentage mortality of larvae, pupae, and emerging adults was recorded at various intervals, usually 24 hour period intervals, throughout the experiments and was the basis for determining the efficacy of the film-forming materials evaluated. The following results were obtained.

TABLE 2

| Test No. | Species | Larval Instar (Days old) | Formulation | Dosage Active (ml/m²) | Cumulative percentage mortality at indicated post-treatment time periods (Hours) | | | | | | |
| --- | --- | --- | --- | --- | --- | --- | --- | --- | --- | --- | --- |
| | | | | | 24 | 48 | 72 | 96 | 120 | 144 | 168 |
| 1 | A.T. | 2nd-3rd (3) | Branched alcohol N | 0.25 | 63 | 80 | 83.3 | 93.3 | 93.3 | 93.3 | 96.7 |
| | | | Isostearyl alcohol | 0.25 | 0 | 3.3 | 16.7 | 40 | 46.7 | 50 | 53.3 |
| | | | Control | — | 0 | 0 | 0 | 3.3 | 3.3 | 3.3 | 3.3 |
| 2 | C.Q. | 2nd-3rd (4) | Branched alcohol N | 0.25 | 6.7 | 43.3 | 53.3 | 60 | 66.7 | 80 | 80* |
| | | | Isostearyl alcohol | 0.25 | 0 | 10 | 13.3 | 13.3 | 13.3 | 13.3 | 26.7* |
| | | | Control | — | 0 | 0 | 0 | 0 | 0 | 0 | 0 |

*adult escape

In general, the above-tabulated bioassay results indicate that β-branched alcohol N is significantly more effective in controlling first-fourth instar larvae of A.T. and C.Q. in RO water and 12.5% sea water than was the comparative isostearyl alcohol. Of importance is the fact that the surface tension reduction of the β-branched alcohol N is substantially higher than the value which the art teaches necessary for such mosquito control as was displayed here.

EXAMPLE 2

Bioassays against larvae of *Aedes taeniorhynchus*, *Aedes aegypti*, *Culex quinquefasciatus*, and *Culex nigripalpus* were conducted with formulations of β-branched alcohol N and its 2 mole ethoxylate and with comparative isostearyl alcohol and its 2 mole ethoxylate. Various combinations of these materials also were evaluated. Tests were conducted in 400 ml glass beakers containing 10-25 first-fourth instar larvae of Aedes or Culex mosquitos and 250 ml of test water (2-3 replications per test series). Controls were used to monitor each test series. A.T. larvae were tested in 12.5% artificial sea water (Instant Ocean ®) while A.T., C.Q. and C.N. larvae were tested in water purified by reverse osmosis filtration (RO). Prior to introduction to the test formulations, larvae in each beaker were fed a few drops of ground rabbit chow-RO water suspension.

Formulations were applied to the surface of water with a microsyringe at the rate of 0.25 ml/m$^2$ (0.26 gal/acre) active ingredient(s). Cumulative percentage mortality of larvae, pupae, and emerging adults was recorded at daily intervals throughout the experiment and is the basis for determining the efficacy of the formulations evaluated.

hol in controlling the mosquitos. In general, formulations of β-branched alcohol N and isostearyl alcohol were not effective (tests 1-4). Similar results (with the exception of test 4) also were obtained with formulations of comparative isostearyl alcohol and its ethoxylate (tests 1-2). The β-branched alcohol N and its ethoxylate appear to exhibit a significantly enhanced larvicidal action when compared to a more linear analog containing the same number of carbon atoms.

EXAMPLE 3

Bioassays against larvae of *Aedes Taeniorhynchus* were conducted with β-branched alcohol N and its 2 mole ethoxylate, and comparative isostearyl alcohol and its 2 mole ethoxylate in water of varying salinities to determine if this water quality parameter would affect the efficacy of the control agents. Tests were conducted in 400 mL glass beakers containing ten second instar larvae of A.T. and 250 mL of test water that varied in salinity from 0 to 25 percent (three replications/test series). Controls were used to monitor the validity of each test series. Eggs of A.T. were hatched in the respective artificial sea water (Instant Ocean ®) concentrations (0, 6.25%, 12.5%, and 25%) and reared to the second instar prior to testing to assure that no adverse osmotic larval reaction would occur. Prior to introduction of the test formulations, larvae in each beaker were

TABLE 3

| Test No. | Species | Larval Instar (Days old) | Formulation | Dosage Active (ml/m$^2$) | Cumulative percentage mortality at indicated post-treatment time periods (Days) | | | | | | |
|---|---|---|---|---|---|---|---|---|---|---|---|
| | | | | | 1 | 2 | 3 | 4 | 5 | 6 | 7 |
| 1 | A.A. | 1st (2) | Isostearyl alcohol | 0.25 | 0 | 5 | 10 | 45 | 50 | 90 | 90 |
| | | | Branched alcohol N | 0.25 | 0 | 10 | 15 | 45 | 70 | 90 | 90 |
| | | | Branched alcohol N: Isostearyl alcohol (50:50) | 0.25 | 9 | 15 | 15 | 75 | 95 | 100 | — |
| | | | Branched alcohol N: Isostearyl alcohol-2EO (50:50) | 0.25 | 0 | 30 | 35 | 55 | 55 | 90 | 90 |
| | | | Control | — | 0 | 0 | 0 | 0 | 0 | 0 | 0 |
| 2 | A.T. | 2nd-3rd (5) | Isostearyl alcohol | 0.25 | 6.7 | 6.7 | 20 | 26.7 | 43.3 | 60 | 63.3 |
| | | | Branched alcohol N | 0.25 | 80 | 93.3 | 96.7 | 96.7 | 96.7 | 96.7 | 96.7 |
| | | | Branched alcohol N: Isostearyl alcohol (50:50) | 0.25 | 0 | 16.7 | 33.3 | 50 | 63.3 | 63.3 | 66.7 |
| | | | Branched alcohol N: Isostearyl alcohol-2EO (50:50) | 0.25 | 3.3 | 20 | 36.7 | 46.7 | 53.3 | 56.7 | 73.3 |
| | | | Control | — | 0 | 0 | 0 | 0 | 0 | 6.7 | 6.7 |
| 3 | C.Q. | 2nd-3rd (5) | Isostearyl alcohol | 0.25 | 0 | 0 | 0 | 0 | 10* | 16.7 | — |
| | | | Branched alcohol N | 0.25 | 0 | 26.7 | 50 | 56.7 | 66.7* | 73.3 | — |
| | | | Branched alcohol N: Isostearyl alcohol (50:50) | 0.25 | 0 | 0 | 0 | 6.7* | 26.7* | 36.7 | — |
| | | | Control | — | 0 | 0 | 0 | 0 | 0 | 0 | — |
| 4 | C.Q. | 3rd-4th/pupae (7-9) | Branched alcohol N: Isostearyl alcohol (50:50) | 0.25 | 0* | 13.3 | 15 | 21.5 | — | 35 | 40* |
| | | | Branched alcohol N: Isostearyl alcohol-2EO (50:50) | 0.25 | 8.3 | 65 | 78.3 | 86.7 | — | 96.7 | 98.3 |
| | | | Control | — | 0 | 0* | 3.3* | 5* | — | 5* | 5* |
| 5 | A.T. | 2nd-3rd (4) | Isostearyl alcohol | 0.25 | 3.3 | 10 | 23.3 | — | — | 50 | 63.3 |
| | | | Branched alcohol N | 0.25 | 26.7 | 63.3 | 90 | — | — | 100 | — |
| 6 | C.N. | 4th (—) | Isostearyl alcohol | 0.25 | 6.7 | 26.7 | 53.3 | — | — | 63.3* | 70 |
| | | | Branched alcohol N | 0.25 | 60 | 76.7 | 90 | — | — | 90* | 90 |
| | | | Control | — | 0 | 3.3 | 3.3* | — | — | 3.3* | — |
| 7 | C.N. | 2nd (2) | Isostearyl alcohol | 0.25 | 16.7 | 23.2 | 26.7 | — | — | 60 | — |
| | | | Branched alcohol N | 0.25 | 20 | 33.3 | 36.7 | — | — | 100 | — |
| | | | Control | — | 0 | 0 | 0 | — | — | 3.3 | — |

*Adult escapes

In general, the above-tabulated results of the bioassays against the Culex and Aedes spp indicated that β-branched alcohol N ethoxylate was more effective in fresh and salt water than the comparative isostearyl alcohol ethoxylate. Similarly, β-branched alcohol was usually more effective than comparative isostearyl alcohol.

fed a few drops of ground rabbit chow suspension. Water temperature in all tests was ca. 26.5° C. Formulations were applied to the surface of the water with a microsyringe (25 gauge needle) at the rate of 0.25 mL/meter$^2$ active ingredient in each test series. The following results were obtained.

TABLE 4

| Test No. | Larval Instar (Days old) | Water Quality (% sea water) | Formulation | Total Dosage Active (Gal/Acre) | Cumulative percentage mortality at indicated post-treatment time periods (Days) | | | |
|---|---|---|---|---|---|---|---|---|
| | | | | | 1 | 2 | 3 | 4 |
| A | 2nd (2) | R.O. (0%) | Isostearyl alcohol-2EO | 0.26 | 0 | 13.3 | 40 | 60 |
| | | | Branched alcohol N—2EO | 0.26 | 3.3 | 66.7 | 100 | — |
| | | | Isostearyl alcohol | 0.26 | 0 | 10 | 26.7 | 56.7 |
| | | | Branched alcohol N | 0.26 | 13.3 | 70 | 70 | 86.7 |
| | | | Control | — | 0 | 0 | 3.3 | 3.3 |
| B | 2nd (2) | 6.25% | Isostearyl alcohol-2EO | 0.26 | 3.3 | 23.3 | 23.3 | 26.7 |
| | | | Branched alcohol N—2EO | 0.26 | 6.7 | 36.7 | 80 | 93.3 |
| | | | Isostearyl alcohol | 0.26 | 3.3 | 23.3 | 33.3 | 40 |
| | | | Branched alcohol N | 0.26 | 16.7 | 60 | 90 | 100 |
| | | | Control | — | 0 | 0 | 0 | 0 |
| C | 2nd (2) | 12.5% | Isostearyl alcohol-2EO | 0.26 | 0 | 0 | 0 | 20 |
| | | | Branched alcohol N—2EO | 0.26 | 3.3 | 53.3 | 5.3 | 100 |
| | | | Isostearyl alcohol | 0.26 | 0 | 3.3 | 10 | 16.7 |
| | | | Branched alcohol N | 0.26 | 3.3 | 60 | 73.3 | 100 |
| | | | Control | — | 0 | 0 | 0 | 03.3 |
| D | 2nd (2) | 25% | Isostearyl alcohol-2EO | 0.26 | 0 | 10 | 20 | 50 |
| | | | Branched alcohol N—2EO | 0.26 | 3.3 | 53.3 | 93.3 | 100 |
| | | | Isostearyl alcohol | 0.26 | 0 | 0 | 6.7 | 13.3 |
| | | | Branched alcohol N | 0.26 | 23.3 | 63.3 | 86.7 | 100 |
| | | | Control | — | 0 | 3.3 | 3.3 | 3.3 |

The above-tabulated results of the bioassays indicate that, with the exception of the 25% sea water level, comparative ethoxylated isostearyl alcohol showed a reduction in larvicidal efficacy with increasing salinity at four days post-treatment. An even more pronounced trend at this time period was noted for the comparative isostearyl alcohol. Significantly greater larvicidal action, with little or no reduction in efficacy with increasing salinity, was noted for the β-branched alcohol N and its two mole ethoxylate. The unexpected larvicidal activity of the β-branched alcohols of the present invention again is demonstrated.

EXAMPLE 4

Bioassays against larvae of A.T. and C.Q. were conducted with branched alcohol M and tridecyl alcohol T to determine its larvicidal and pupicidal activity. Initial tests were conducted in 400 mL glass beakers containing ten second-fourth instar larvae of the Aedes or Culex mosquitos in 250 mL of test water (three replications/formulation). Controls were used to monitor the validity of each test series. C.Q. larvae were evaluated in well water purified by reverse osmosis filtration while larvae of A.T. were tested in 12.5% artificial sea water (Instant Ocean ®). Prior to introduction of the candidate formulations, larvae in each beaker were fed a few drops of ground rabbit chow-RO water suspension. Water temperature in all tests was ca. 26.5° C. Candidate formulations were applied to the surface of the water with a microsyringe (25 gauge needle) at a rate of 0.25 mL/meters$^2$ in each test series. The following results were obtained.

TABLE 5

| Test No. | Species | Larval Instar (Days Old) | Formulation | Total Dosage Active (Gal/acre) | Cumulative percentage mortality at indicated post-treatment time periods (Days) | | | | |
|---|---|---|---|---|---|---|---|---|---|
| | | | | | 1 | 2 | 3 | 4 | 6 |
| 1 | C.Q. | 4th (8) | Branched alcohol M | 0.26 | 93.3 | 93.3 | — | — | — |
| | | | Tridecyl alcohol T | 0.26 | 86.7 | 86.7 | — | — | — |
| | | | Control | — | 0 | 3.3 | — | — | — |
| 2 | A.T. | 2nd–3rd (3) | Branched alcohol M | 0.26 | 33.3 | 93.3 | 93.3 | 100 | — |
| | | | Tridecyl alcohol T | 0.26 | 76.7 | 100 | — | — | — |
| | | | Control | — | 0 | 0 | 0 | 3.3 | — |
| 3 | A.T. | 2nd–3rd (4) | Branched alcohol M | 0.26 | 3.3 | 10 | 20 | 40 | 60 |
| | | | Tridecyl alcohol T | 0.26 | 13.3 | 50 | 53.3 | 70 | 90 |
| | | | Control | — | 0 | 0 | 0 | 0 | |

In fresh water against C.Q. (Test No. 1) branched alcohol M and tridecyl alcohol T displayed excellent efficacy. It should be noted, however, that as a general rule, unethoxylated alcohols do not spread or respread over the surface of the water as rapidly as their ethoxylated counterparts. In salty water against A.T. (Tests 2-3), tridecyl alcohol T showed greater efficacy than branched alcohol M, though both alcohols were effective in controlling larvae of A.T. These tests indicate the unexpected efficacy which the β-branched alkanols of the present invention provide in controlling the mosquito population. Such efficacy is unexpected in view of the teachings in the art.

EXAMPLE 5

Laboratory evaluations against first-fourth instar larvae of A.A., C.Q., and A.T. were conducted with formulations of various branched alcohols and their ethoxylates to determine the comparative larvicidal/pupacidal action of such formulations. Bioassays were conducted in 400 ml glass beakers containing 10 first-fourth instar larvae of Aedes or Culex spp and 250 ml of test water (three replications/formulation). Controls were used to monitor the validity of each test series. C.Q. and A.A. larvae were evaluated in well water purified by reverse osmosis filtration while larvae of A.T. were tested in 12.5% artificial sea water (Instant Ocean). Prior to introduction of the candidate formulations, larvae in each beaker were fed a few drops of ground rabbit chow-RO water suspension. Water temperature in all tests was ca. 26.5° C.

Candidate formulations were applied to the surface of the water with a microsyringe equipped with a 25 gauge needle at a rate of 0.25 ml/m² (i.e. 0.26 gallons formulation/surface acre) in each test series. The following results were recorded.

TABLE 6

| Test No. | Species | Larval Instar (Days old) | Formulation | Dosage Active (ml/m²) | Cumulative percentage mortality at indicated post-treatment time periods (Days) | | | | | | | | |
|---|---|---|---|---|---|---|---|---|---|---|---|---|---|
| | | | | | 1 | 2 | 3 | 4 | 5 | 6 | 7 | 8 | 9 |
| 1 | C.Q. | 4th (7) | Isostearyl alcohol | 0.25 | 6.7 | 73.3 | 83.3 | 83.3 | — | 100 | — | | |
| | | | Branched alcohol M | 0.25 | 30 | 73.3 | 100 | — | — | — | — | | |
| | | | Branched alcohol T | 0.25 | 43.3 | 66.7* | 66.7 | 66.7 | — | 76.7* | — | | |
| | | | Branched alcohol H | 0.25 | 30 | 93.3 | 96.7 | 100 | — | — | — | | |
| | | | Branched alcohol N—2EO | 0.25 | 46.7 | 100 | — | — | — | — | — | | |
| | | | Branched alcohol M—2EO | 0.25 | 40 | 93.3 | 96.7 | 100 | — | — | — | | |
| | | | Branched alcohol T—2EO | 0.25 | 43.3 | 90 | 93.3 | 93.3 | — | 100 | — | | |
| | | | Branched alcohol H—2EO | 0.25 | 63.3 | 80 | 90 | 96.7 | — | 100 | — | | |
| | | | Isostearyl alcohol-2EO | 0.25 | 16.7 | 90 | 100 | — | — | — | — | | |
| | | | Control | — | 0 | 0* | — | — | — | 0* | — | | |
| 2 | A.T. | 3rd–4th (5) | Isostearyl alcohol | 0.25 | 56.7 | 66.7 | 73.3 | 93.3 | — | 100 | — | | |
| | | | Branched alcohol M | 0.25 | 10 | 33.3* | 50 | 50 | — | 96.7 | 96.7 | | |
| | | | Branched alcohol T | 0.25 | 40 | 93.3 | 93.3 | 93.3 | — | 100 | — | | |
| | | | Branched alcohol H | 0.25 | 23.3 | 33.3 | 53.3 | 56.7 | — | 100 | — | | |
| | | | Branched alcohol N—2EO | 0.25 | 33.3 | 86.7 | 93.3 | 93.3 | — | 100 | — | | |
| | | | Branched alcohol M—2EO | 0.25 | 6.7 | 43.3 | 73.3 | 86.7 | — | 100 | — | | |
| | | | Branched alcohol T—2EO | 0.25 | 26.7 | 46.7 | 76.7 | 76.7* | — | 96.7 | 96.7 | | |
| | | | Branched alcohol H—2EO | 0.25 | 16.7 | 36.7 | 60 | 83.3 | — | 96.7 | 100 | | |
| | | | Isostearyl alcohol-2EO | 0.25 | 20 | 23.3 | 40 | 50 | — | 56.7 | 100 | | |
| | | | Control | — | 0 | 0* | 0 | 0 | — | 3.3 | 3.3* | | |
| 3 | C.Q. | 4th (8) | Isostearyl alcohol | 0.25 | 0 | 50* | 56.7* | 56.7* | — | 60* | — | | |
| | | | Branched alcohol M | 0.25 | 6.7 | 13.3* | 13.3* | — | — | — | — | | |
| | | | Branched alcohol T | 0.25 | 26.7 | 46.7* | 56.7* | 56.7* | — | — | — | | |
| | | | Branched alcohol N—2EO | 0.25 | 86.7 | 100 | — | — | — | — | — | | |
| | | | Branched alcohol M—2EO | 0.25 | 23.3 | 90 | 96.7 | 100 | — | — | — | | |
| | | | Branched alcohol T—2EO | 0.25 | 86.7 | 100 | — | — | — | — | — | | |
| | | | Branched alcohol H—2EO | 0.25 | 43.3 | 90 | 100 | — | — | — | — | | |
| | | | Isostearyl alcohol-2EO | 0.25 | 10 | 53.3 | 90 | 100 | — | — | — | | |
| | | | Control | — | 0 | 0* | 0* | 0* | — | — | 0* | | |
| 4 | A.A. | 3rd–4th (5) | Isostearyl alcohol | 0.25 | 3.3 | 3.3 | 23.3* | 30* | — | 53.3* | 53.3* | | |
| | | | Branched alcohol M | 0.25 | 3.3 | 6.7 | 6.7* | 20* | — | 26.7* | 30* | | |
| | | | Branched alcohol T | 0.25 | 23.3 | 33.3 | 46.7* | 50* | — | 60 | 60* | | |
| | | | Branched alcohol H | 0.25 | 16.7 | 33.3* | 46.7* | 60* | — | 63.3 | 63.3* | | |
| | | | Branched alcohol N—2EO | 0.25 | 26.7 | 40 | 50 | 63.3 | — | 100 | — | | |
| | | | Branched alcohol M—2EO | 0.25 | 20 | 46.7 | 66.7 | 76.7 | — | 96.7 | 96.7 | | |
| | | | Branched alcohol T—2EO | 0.25 | 20 | 33.3 | 70 | 76.7 | — | 96.7 | 96.7 | | |
| | | | Branched alcohol H—2EO | 0.25 | 23.3 | 33.3 | 50 | 70 | — | 83.3 | 83.3 | | |
| | | | Isostearyl alcohol-2EO | 0.25 | 3.3 | 30 | 50 | 63.3 | — | 73.3 | 73.3 | | |
| | | | Control | — | 0 | 0 | 3.3* | 3.3 | — | 3.3 | 3.3* | | |
| 5 | C.Q. | 1st (1) | Isostearyl alcohol | 0.25 | 0 | 0 | 6.7 | — | — | 20 | 40 | 70 | — |
| | | | Branched alcohol M | 0.25 | 0 | 0 | 3.3 | — | — | 6.7 | 36.7 | 36.7 | — |
| | | | Branched alcohol M | 0.25 | 0 | 0 | 3.3 | — | — | 16.7 | 16.7 | 20 | — |
| | | | Branched alcohol H | 0.25 | 0 | 3.3 | 3.3 | — | — | 10 | 33.3 | 76.7 | — |
| | | | Branched alcohol N—2EO | 0.25 | 3.3 | 6.7 | 10 | — | — | 26.7 | 26.7 | 50 | — |
| | | | Branched alcohol M—2EO | 0.25 | 0 | 0 | 6.7 | — | — | 6.7 | 13.3 | 50 | — |
| | | | Branched alcohol T—2EO | 0.25 | 0 | 3.3 | 6.7 | — | — | 16.7 | 20 | 53.3 | — |
| | | | Branched alcohol H—2EO | 0.25 | 0 | 0 | 3.3 | — | — | 3.3 | 6.7 | 46.7 | — |
| | | | Isostearyl alcohol-2EO | 0.25 | 0 | 0 | 0 | — | — | 0 | 13.3 | 13.3 | — |
| | | | Control | — | 0 | 0 | 0 | — | — | 0 | 0 | 20 | — |
| 6 | A.T. | 1st (1) | Isostearyl alcohol | 0.25 | 0 | 0 | 6.7 | — | 23.3 | 100 | — | — | — |
| | | | Branched alcohol M | 0.25 | 3.3 | 13.3 | 20 | — | 63.3 | 83.3 | 90 | 100 | — |
| | | | Branched alcohol T | 0.25 | 3.3 | 10 | 23.3 | — | 30 | 50 | 80 | 100 | — |
| | | | Branched alcohol H | 0.25 | 6.7 | 16.7 | 30 | — | 60 | 83.3 | 83.3 | 100 | — |
| | | | Branched alcohol N—2EO | 02.5 | 3.3 | 20 | 43.3 | — | 56.7 | 100 | — | — | — |
| | | | Branched alcohol M—2EO | 0.25 | 0 | 10 | 16.7 | — | 30 | 70 | 96.7 | 100 | — |
| | | | Branched alcohol T—2EO | 0.25 | 36.7 | 66.7 | 93.3 | — | 100 | — | — | — | — |
| | | | Branched alcohol H—2EO | 0.25 | 3.3 | 13.3 | 16.7 | — | 20 | 70 | 90 | 93.3 | 100 |
| | | | Isostearyl alcohol-2EO | 0.25 | 0 | 13.3 | 16.7 | — | 23.3 | 60 | 80 | 100 | — |
| | | | Control | — | 0 | 0 | 0 | — | 0 | 0 | 0 | 0 | 0 |
| 7 | A.A. | 4th (7) | Isostearyl alcohol | 0.25 | 6.7 | 10 | 30* | 43.3* | — | 43.3* | — | — | — |
| | | | Branched alcohol M | 0.25 | 0 | 3.3 | 3.3* | 16.7* | — | — | — | — | — |
| | | | Branched alcohol T | 0.25 | 3.3 | 3.3 | 3.3* | 3.3* | — | 6.7* | 6.7* | — | — |
| | | | Branched alcohol H | 0.25 | 0 | 3.3 | 20* | 43.3* | — | 50* | — | — | — |
| | | | Branched alcohol N—2EO | 0.25 | 36.7 | 56.7 | 73.3 | 90 | — | 100 | — | — | — |
| | | | Branched alcohol T—2EO | 0.25 | 0 | 0 | 43.3 | 53.3* | — | 73.3 | 76.7 | — | — |
| | | | Branched alcohol H—2EO | 0.25 | 6.7 | 10 | 56.7 | 90 | — | 100 | — | — | — |
| | | | Isostearyl alcohol-2EO | 0.25 | 0 | 16.7 | 63.3 | 90 | — | 100 | — | — | — |
| | | | Control | — | 3.3 | 3.3 | 3.3* | 3.3* | — | 3.3* | 3.3* | — | — |

*Adult escapes indicated.

In general, the β-branched alkanols displayed somewhat inconsistent efficacy when evaluated against the larval stages of mosquitos. The ethoxylated versions, however, provided more consistent results. The results reported for comparative isostearyl alcohol are suspect based upon the data reported in the other examples.

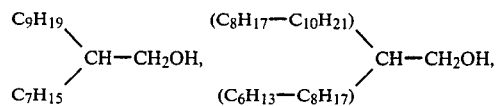 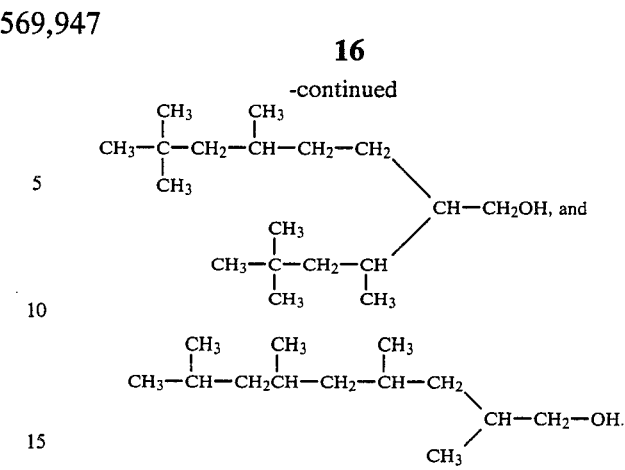

We claim:

1. A method for controlling mosquitos which comprises coating the surface of a body of water containing immature forms of mosquitos with an effective amount of one or more of a β-branched alkanol or a 1–3 mole alkoxylate thereof, said β-branched alkanol having the following structure:

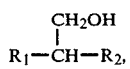

where
$R_1$ and $R_2$ are $C_9$–$C_{28}$; and
$R_1$ or $R_2$ are at least $C_3$ or
$R_2$ is $CH_3$ and $R_1$ contains at least two branch sites, said alkanol reducing the surface tension of the body of water to greater than about 35 dynes/cm.

2. The method of claim 1 wherein said β-branched alkanol reduces the surface tension of said body of water to between about 40 and 50 dynes/cm.

3. The method of claim 1 wherein said β-branched alkanol is a Guerbet alkanol wherein $R_1$ contains two carbon atoms more than $R_2$.

4. The method of claim 1 wherein said β-branched alkanol is represented by the following structure:

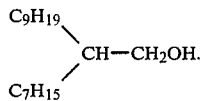

5. The method of claim 1 wherein said β-branched alkanol is represented by the following structure:

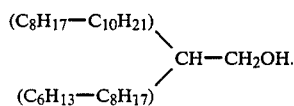

6. The method of claim 1 wherein said β-branched alkanol is represented by the following structure:

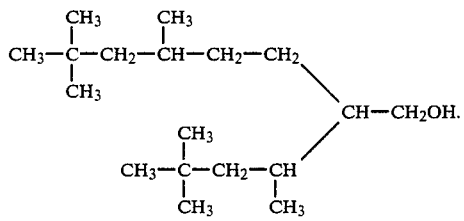

7. The method of claim 1 wherein said β-branched alkanol is represented by the following structure:

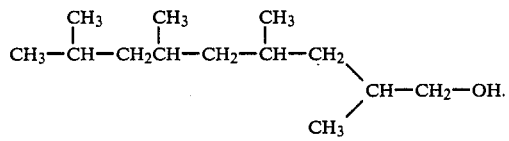

8. The method of claim 1 wherein said surface is coated with an effective amount of said 1–3 mole alkoxylate of said β-branched alkanol.

9. The method of claim 8 wherein said alkoxylate is a 1–3 mole ethoxylate of said β-branched alkanol.

10. The method of claim 9 wherein said β-branched alkanol of said 1–3 moles ethoxylate is a Guerbet alkanol wherein $R_1$ contains two carbon atoms more than $R_2$.

11. The method of claim 9 wherein said β-branched alkanol of said 1–3 mole ethoxylate is represented by the following structure:

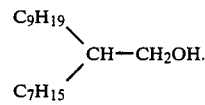

12. The method of claim 9 wherein said β-branched alkanol of said 1–3 mole ethoxylate is represented by the following structure:

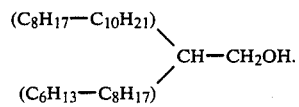

13. The method of claim 9 wherein said β-branched alkanol of said 1–3 mole ethoxylate is represented by the following structure:

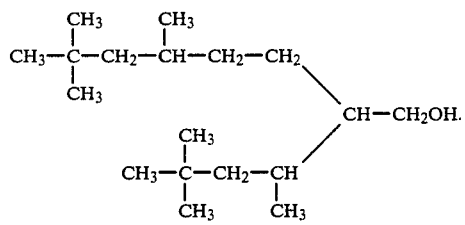

14. The method of claim 9 wherein said β-branched alkanol of said 1–3 mole ethoxylate is represented by the following structure:

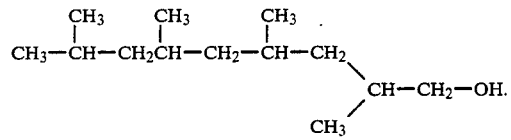

15. The method of claim 1 wherein said surface is coated with an effective amount of a mixture of said β-branched alkanol and a 1–3 mole alkoxylate of said β-branched alkanol.

16. The method of claim 15 wherein said alkoxylate comprises the 1–3 mole ethoxylate of said β-branched alkanol.

17. The method of claim 16 wherein said β-branched alkanol is a Guerbet alkanol, wherein $R_1$ contains two more carbon atoms than $R_2$.

18. The method of claim 16 wherein said β-branched alkanol is selected from the group consisting of β-branched alkanols represented by the following structures and mixtures thereof: